United States Patent [19]
Byerly et al.

[11] Patent Number: 6,067,524
[45] Date of Patent: May 23, 2000

[54] METHOD AND SYSTEM FOR AUTOMATICALLY GENERATING ADVISORY INFORMATION FOR PHARMACY PATIENTS ALONG WITH NORMALLY TRANSMITTED DATA

[75] Inventors: Baxter H. Byerly, St. Petersburg, Fla.; Robert Anthony Uecker, Chesterfield, Mo.

[73] Assignee: Catalina Marketing International, Inc., St. Petersburg, Fla.

[21] Appl. No.: 09/226,209

[22] Filed: Jan. 7, 1999

[51] Int. Cl.$^7$ ..................................................... G06F 17/60
[52] U.S. Cl. ..................... 705/3; 705/1; 705/2; 705/14; 706/924
[58] Field of Search ................................. 705/3, 2, 1, 14; 706/924

[56] References Cited

U.S. PATENT DOCUMENTS

| | | | |
|---|---|---|---|
| 3,921,196 | 11/1975 | Patterson | 235/375 |
| 4,554,446 | 11/1985 | Murphy et al. | 235/487 |
| 4,672,377 | 6/1987 | Murphy et al. | 340/825.34 |

(List continued on next page.)

FOREIGN PATENT DOCUMENTS

WO 98/38589    9/1998    WIPO .

OTHER PUBLICATIONS

Chain Store Age, vol. 73, No. 8, pp. 45–46 and 48, Lebhar–Friedman, "CVS Writes Its Own Systems Script", Aug. 1997.

Youji Kohda, et al., Computer Networks and ISDN Systems, vol. 28, No. 11, pp. 1493–1499, "Ubiquitous Advertising On The WWW: Merging Advertisement on the Browser", May 1996.

Disclosure by Applicants filed in related application serial number 08/764,139 signed by Baxter H. Byerly and dated Jul. 15, 1999.

Henry Gilgoff, "It's Your Money/Prescription: Get It In Writing", Newsday, Aug. 11, 1996, 3 pages.

"Envoy links with pharmacies", The Tennessean, Jul. 27, 1996, 1 page.

(List continued on next page.)

*Primary Examiner*—Allen R. MacDonald
*Assistant Examiner*—Akiba Robinson-Boyce
*Attorney, Agent, or Firm*—Oblon, Spivak, McClelland, Maier & Neustadt, P.C.

[57] ABSTRACT

A method and system for generating advisory messages to pharmacy patients includes appending patient-specific information to a data record containing normally transmitted information. The data record is transmitted between a third party computer and a pharmacy computer during a pharmacy transaction. The data record transmitted to the pharmacy computer is captured by an advisory computer as the data record is received by the pharmacy computer or after the data record is transmitted to the pharmacy computer, and the patient-specific information is extracted from the captured data record. The advisory computer generates an advisory message based on the extracted patient-specific information, and it transmits the generated advisory message to a pharmacy printer. The advisory computer includes a memory containing a data structure for storing the patient-specific information, the normally transmitted information, and the generated advisory message. A computer program product includes a computer storage medium and a computer program code mechanism embedded in the computer storage medium for causing a computer to generate an advisory message. The computer program code mechanism includes a first computer code device configured to append the patient-specific information, a second computer code device configured to capture the data record transmitted to the pharmacy computer, a third computer code device configured to extract the patient-specific information from the captured data record, a fourth computer code device configured to generate the advisory message based on the extracted patient specific information, and a fifth computer code device configured to transmit the generated advisory message to the pharmacy printer.

16 Claims, 5 Drawing Sheets

U.S. PATENT DOCUMENTS

| | | | |
|---|---|---|---|
| 4,673,802 | 6/1987 | Ohmae et al. | 705/17 |
| 4,674,041 | 6/1987 | Lemon et al. | 705/14 |
| 4,695,954 | 9/1987 | Rose et al. | 221/15 |
| 4,723,212 | 2/1988 | Mindrum et al. | 705/14 |
| 4,785,969 | 11/1988 | McLaughlin | 221/2 |
| 4,847,764 | 7/1989 | Halvorson | 364/479.01 |
| 4,908,761 | 3/1990 | Tai | 705/14 |
| 4,910,672 | 3/1990 | Off et al. | 705/14 |
| 4,991,877 | 2/1991 | Lieberman | 283/36 |
| 5,056,019 | 10/1991 | Schultz et al. | 705/14 |
| 5,256,863 | 10/1993 | Ferguson et al. | 380/24 |
| 5,299,121 | 3/1994 | Brill et al. | 600/301 |
| 5,305,196 | 4/1994 | Deaton et al. | 705/10 |
| 5,353,218 | 10/1994 | De Lapa et al. | 705/14 |
| 5,515,270 | 5/1996 | Weinblatt | 705/14 |
| 5,597,995 | 1/1997 | Williams et al. | 235/375 |
| 5,621,812 | 4/1997 | Deaton et al. | 382/100 |
| 5,638,457 | 6/1997 | Deaton et al. | 382/100 |
| 5,644,723 | 7/1997 | Deaton et al. | 705/14 |
| 5,649,114 | 7/1997 | Deaton et al. | 705/14 |
| 5,659,469 | 8/1997 | Deaton et al. | 705/14 |
| 5,659,741 | 8/1997 | Eberhardt | 707/104 |
| 5,666,492 | 9/1997 | Rhodes et al. | 705/3 |
| 5,700,998 | 12/1997 | Palti | 235/375 |
| 5,703,786 | 12/1997 | Conkright | 364/479.14 |
| 5,715,293 | 2/1998 | Mahoney | 379/23 |
| 5,737,396 | 4/1998 | Garcia | 379/88.16 |
| 5,737,539 | 4/1998 | Edelson | 705/3 |
| 5,758,095 | 5/1998 | Albaum et al. | 705/2 |
| 5,774,868 | 6/1998 | Cragun et al. | 705/10 |
| 5,799,981 | 9/1998 | Tung et al. | 283/56 |
| 5,803,498 | 9/1988 | Tung et al. | 283/56 |
| 5,822,544 | 10/1998 | Chaco et al. | 705/2 |
| 5,823,948 | 10/1998 | Ross, Jr. et al. | 600/300 |
| 5,827,180 | 10/1998 | Goodman | 600/300 |
| 5,832,449 | 11/1988 | Cunningham | 705/3 |
| 5,832,457 | 11/1998 | O'Brien et al. | 705/14 |
| 5,832,488 | 11/1998 | Eberhardt | 707/10 |
| 5,835,455 | 11/1998 | Hanson et al. | 368/10 |
| 5,845,255 | 12/1998 | Mayaud | 705/3 |
| 5,845,264 | 12/1998 | Nellhaus | 705/28 |
| 5,850,344 | 12/1998 | Conkright | 364/479.01 |
| 5,855,395 | 1/1999 | Foote et al. | 283/67 |
| 5,867,821 | 2/1999 | Ballantyne et al. | 705/2 |
| 5,884,273 | 3/1999 | Sattizahn et al. | 705/3 |
| 5,899,998 | 5/1999 | McGauley et al. | 707/104 |

OTHER PUBLICATIONS

"ProxyMed Expands Its Electronic Scripts Reach", Health Data Network News, Nov. 6, 1995, 2 pages.

"The Pharmacy Fund Announces Strategic Alliance With Software Vendors To Provide Seamless Access To Rapid Rxemit; High–Tech Rapid Rxemit Financial Service Improves Cash Flow For Pharmacists", Business Wire, Jul. 15, 1996, 3 pages.

Michael F. Conlan, "In–Your–Face Pharmacy", Drug Topics, Jul. 8, 1996, 8 pages.

Annmarie Sarsfield, "Seniors touch screens to access medical facts The Agency for Health Care Administration will place free–standing, easy to use computers in Pinellas for a 3–month trial period", The Tampa Tribune, May 21, 1996, 2 pages.

Michael Wilke, "Actmedia Tries Coupons in Pharmacies", Advertising Age, May 6, 1996, 1 page.

"Software Supplement Your Pharmacy Practice", Computer Talk, vol. 16 No. 3, May/Jun. 1996, 10 pages.

"Pharmacies bolster marketing", Chain Drug Review, May 6, 1996, 2 pages.

"Medi–Span Enters Coupon Business With Target Rx", By Medi–Span, May 1996, 1 page.

"Neuman Distributors, Inc. Launches Interactive Kiosks Offering Consumers Information And High Value Instant Coupons", PR Newswire, Apr. 15, 1996, 2 pages.

Robin Foote—President, "Medi–Link $^{SM}$ Coupon System Rolls–out at Wakefern, Snyder, May's, and Pharmhouse", Medi–Link, Apr. 11, 1996, 13 pages.

Doran Froke, "AdAge Daily Fax" ActMedia, Apr. 9, 1996, 2 pages.

"Healthpoint Introduces Clinical Information System To Increase Practice Productivity And Enhance Care, Healthpoint Acs Unveiled At Himss Annual Convention", Business Wire, Mar. 5, 1996, 3 pages.

"Coupon Vehicles Set for Pharmacies", Information Technology, Jan. 15, 1996, 1 page.

Pat Natschke Lenius, "Coupon vehicles set for pharmacies. (Newsletters to be given to consumers of certain pharmaceuticals)", Supermarket News, Jan. 15, 1996, 2 pages.

CounseLabels, Liberty Bell Pharmacy, Jan. 11, 1996, 1 page.

"Medi–Link Offers Point–Of–CareCoupon Promotions", Creative, Dec. 1, 1995, 1 page.

Greg Muirhead, "Computer support", Nov. 6, 1995, 1 page.

Christina Veiders, "Retailers expanding health information/coupon systems. (Health Resource and Medi–Link)", Supermarket News, Oct. 9, 1995, 2 pages.

Michael Slezak, "Programming pharmacy's future", American Druggist, Oct. 1, 1995, 8 pages.

"Drug Emporium adopts Rx system", Chain Drug Review, Sep. 25, 1995, vol. 17, No. 18, 1 page.

"The Pharmacy Field Remains Split Over An Electronic Prescription Standard", Automated Medical Payments News, Aug. 20, 1995, 2 pages.

"National Data Corporation Announces Affiliation With National Network Of Preferred Vendors", PR Newswire, Jun. 5, 1996, 2 pages.

"Grocers Check Out High Tech To Survive", Advertising Age, May 8, 1995, 1 page.

"Drug Emporium Tries Out Medi–Link Coupon System", RX Marketplace, May 1, 1995, 1 page.

David Vaczek, "Kroger, Wakefern Testing Pharmacy Coupon Systems", Pharmacy Retailing, Apr. 1995, 1 page.

"Prescription Pharmaceuticals and Biotechnology", F–D–C Reports, Apr. 24, 1995, vol. 57, No. 17, 1 page.

"Health product manufacturers using interactive P–O–P. (Point–of purchase marketing)", Potentials in Marketing, Mar. 1, 1995, 2 pages.

Allen Symons, "Do–it–yourself shopping at its best. (Home Select kiosk)", Drug Store News, Feb. 6, 1995, 2 pages.

Jennifer Reingold, "Cardinal rule. (Drug wholesaler Cardinal Health; includes related article)", Financial World, Jan. 31, 1995, 5 pages.

Tina Cassidy, "Confusion reigns over checking and credit card law", P&L Publication Inc. Boston Business Journal, Apr. 6, 1992, pp. 7–10.

Bob Mannarino, "The schedule of the presentations at the May 1991 FMI Chicago Conference and the Mannarino publication", May 6, 1991, 21 pages.

"Point of Scan, Electronic Frequent Shopper Programs", Jan. 1991, 3 pages.

Mollie Neal, "Quaker's direct hit; Quaker Oats Co.'s advertising subsidiary Quaker Direct", Hoke Communications Inc. Direct Marketing, Jan. 1991, pp. 3–6.

Sue Lawmaster, "Checkout Savings System and Frequency Marketing Overview", Catalina publication, Dec. 10, 1990, 34 pages.

Tom Wilson, "Market Imaging Systems, Inc. / Catalina Marketing Corporation", Sep. 18, 1990, 21 pages.

"Frequency Programs: Cashing In On Promotions", The Marketing Institute, Sep. 11 & 12, 1990, pp. 1–38.

Cathy Cebulski, "P&G, Central Trust develop electronic marketing system", The Greater Cincinnati Business Group, Mar. 26–Apr. 1, 1990, 1 page.

Michael McDermott, "Supermarkets become marketing–driven for the 1990's", Adweek's Marketing Week v31, n12, p50, 2 pages.

"Bar Codes Capture Info", Target Marketing, v12, n1, p. 52, 1 page.

Martha Groves, "Frequent–Shopper Plans Are Wooing Consumers", Los Angeles Times, Oct. 1, 1989, 4 pages.

Michael Gates, "The Unfulfilled Promise", Incentive, Database Marketing, Sep. 1989, p. 123–130.

"Scanning a New Horizon; Food Research Through Computerized Frequent Buyer Programs", Aug. 1989, pp. 16–18.

"Bar Codes Capture Info", Target Marketing, Jan. 1989, v12, n1, p52, 1 page.

Richard Schulman, "Electronic Marketing: a big stakes game for the retailer and manufacturer", Supermarket Business, v43, n2, p21, 3 pages.

METHOD AND SYSTEM FOR AUTOMATICALLY GENERATING ADVISORY INFORMATION FOR PHARMACY PATIENTS ALONG WITH NORMALLY TRANSMITTED DATA

CROSS REFERENCES TO RELATED APPLICATIONS

The present invention is related to commonly owned U.S. Pat. Nos. 4,723,212; 4,910,672; 5,173,851; and 5,612,868 and to commonly owned U.S. patent application Ser. Nos. 08/764,139; and 08/953,646; all of which are incorporated herein by reference.

BACKGROUND OF THE INVENTION

1. Field of the Invention

This invention related generally to point-of-sale systems for use in pharmacies and, more specifically, to systems for automatically generating advisory and/or other information for distribution to pharmacy patients.

2. Discussion of Background

In recent years, various systems have been used to distribute advisory and other information to pharmacy patients based principally on the identification of a prescription drug being purchased. Prescription drugs in the United States are uniquely identifiable by a National Drug Code (NDC). The NDC for a prescription drug is typically entered into a computer terminal by a pharmacist at the time of sale, and it may be encoded on the product itself in bar-code form. Other prescription drug identification systems are employed in other countries, but the principle is the same: to provide a unique code for each prescription drug dispensed by the pharmacy. Based on the nature of the drug, a computer at the point of sale may be used (1) to generate advisory messages to the patient, some of which may be required by governmental regulation and/or (2) to generate promotional materials concerning related or complementary products sold in the pharmacy.

Although such systems available prior to the present invention are satisfactory for some purposes, the advisory messages they provide are not always appropriately focused on the probable needs of the patients purchasing the drugs.

In addition, the systems available prior to the present invention do not provide a means for transmitting information to a patient from a concerned third party, such as a Health Maintenance Organization (HMO), a Preferred Provider Organization (PPO), etc.

Moreover, the systems existing and proposed prior to the present invention typically require major software or hardware changes to existing pharmacy computer systems, the principal function of which is to print prescription labels, simple advisory messages, and billing information. Ideally, additional functions should be provided without the need for major modification of existing pharmacy computer systems.

In addition, most systems available prior to the present invention do not appropriately target the advisory information, except to the extent that information may be provided based on the identification of the prescribed drug.

OBJECTS OF THE INVENTION

Accordingly, one object of this invention is to provide a novel method and system for generating advisory and other information custom-tailored for each patient.

Another object of the present invention to provide a novel method and system for generating advisory and other information without major modification of an existing pharmacy computer system.

It is also an object of the present invention to provide a novel method and system for generating advisory and other information custom-tailored for each patient integrated with information from a third party, such as an HMO, PPO, etc.

It is further object of the present invention to provide a novel method and system for generating advisory and other information without major modification of an existing computer system of a third party, such as an HMO, PPO, etc.

SUMMARY OF THE INVENTION

The above and other objects are achieved according to the present invention by providing a new and improved method and system for generating advisory messages to pharmacy patients. The method includes appending patient-specific information to a data record containing normally transmitted information at a third party computer and transmitting the data record between the third party computer and a pharmacy computer during a pharmacy transaction. The data record transmitted to the pharmacy computer is captured by an advisory computer as the data record is received by the pharmacy computer or after the data record is transmitted by the pharmacy computer, and the patient-specific information is extracted from the captured data record. The advisory computer generates an advisory message based on the extracted patient-specific information, it transmits the generated advisory message to a pharmacy printer, and the pharmacy printer prints the advisory message.

In another aspect of the present invention, the advisory computer includes a memory containing a data structure for storing the patient-specific information, the normally transmitted information, and the generated advisory message.

In a further aspect of the present invention, there is provided a computer program product including a computer storage medium and a computer program code mechanism embedded in the computer storage medium for causing a computer to generate an advisory message. The computer program code mechanism includes a first computer code device configured to append the patient-specific information, a second computer code device configured to capture the data record transmitted to the pharmacy computer, a third computer code device configured to extract the patient specific information from the captured data record, a fourth computer code device configured to generate the advisory message based on the extracted patient-specific information, and a fifth computer code device configured to transmit the generated advisory message to the pharmacy printer. Moreover, this goal is achieved without major modification of the existing third party and/or pharmacy computer systems.

In the context of the present invention, the terms "message" and "advisory message" include all types of information provided to pharmacy patients, including information about the prescribed product being dispensed, information about related products or procedures, patient-specific information (such scheduling of appointments, physicals etc.), promotional materials and/or discount information pertaining to the purchase of prescription products and/or other products, and/or simply news items pertaining to the dispensed product and/or to pharmaceutical products and/or health in general. The information may take the form of multiple-color, two-sided papers, a newsletter, etc., depending on the available printer technology. Some of the information may be generated as a result of a patient condition inferred from other factors, such as the patient's age and the type of medication prescribed. That information may be provided by a third party, such as an HMO, PPO, etc.

The hardware interface in the advisory computer system may take any of various forms, depending primarily on the configuration of the existing pharmacy and third party computer systems. For example, if the pharmacy and/or third party computer systems output data in a parallel format, in a serial format, as a modem transaction, etc., the hardware interface would include appropriate hardware for extracting information from the transmitted data and for transferring the generated advisory message for printing on the pharmacy printer. The hardware interface would further include logic for mediating printer conflicts arising between print data transmitted from the pharmacy computer system and the advisory computer system.

It will be appreciated from the foregoing that the present invention represents a significant advance in providing information to pharmacy patients from third parties, such as HMOs and PPOs. In particular, more targeted information can be provided in an automatic and convenient manner, without having to make significant modifications to existing third party and pharmacy computer systems. Another important advantage of the invention is that, because it "eavesdrops" passively to obtain data from the pharmacy computer and/or third party computer systems' print stream, any malfunction in the advisory computer system does not affect operation of the pharmacy and/or third party computer systems, which can continue to process prescriptions and to print labels.

The present invention pertains to a system and a related method for automatically providing advisory information to pharmacy patients based on (1) the identification of the drugs being dispensed and/or (2) other information pertaining to the patient and to the prescription and/or (3) patient-specific information provided by a third party, such as an HMO, PPO, etc.

Other aspects and advantages of the invention will become apparent from the more detailed description that follows, taken in conjunction with the drawings, which are briefly described below.

BRIEF DESCRIPTION OF THE DRAWINGS

A more complete appreciation of the invention and many of the attendant advantages thereof will be readily obtained as the same becomes better understood by reference to the following detailed descriptions when considered in connection with the accompanying drawings, wherein.

DESCRIPTION OF THE PREFERRED EMBODIMENTS

Figure 1:
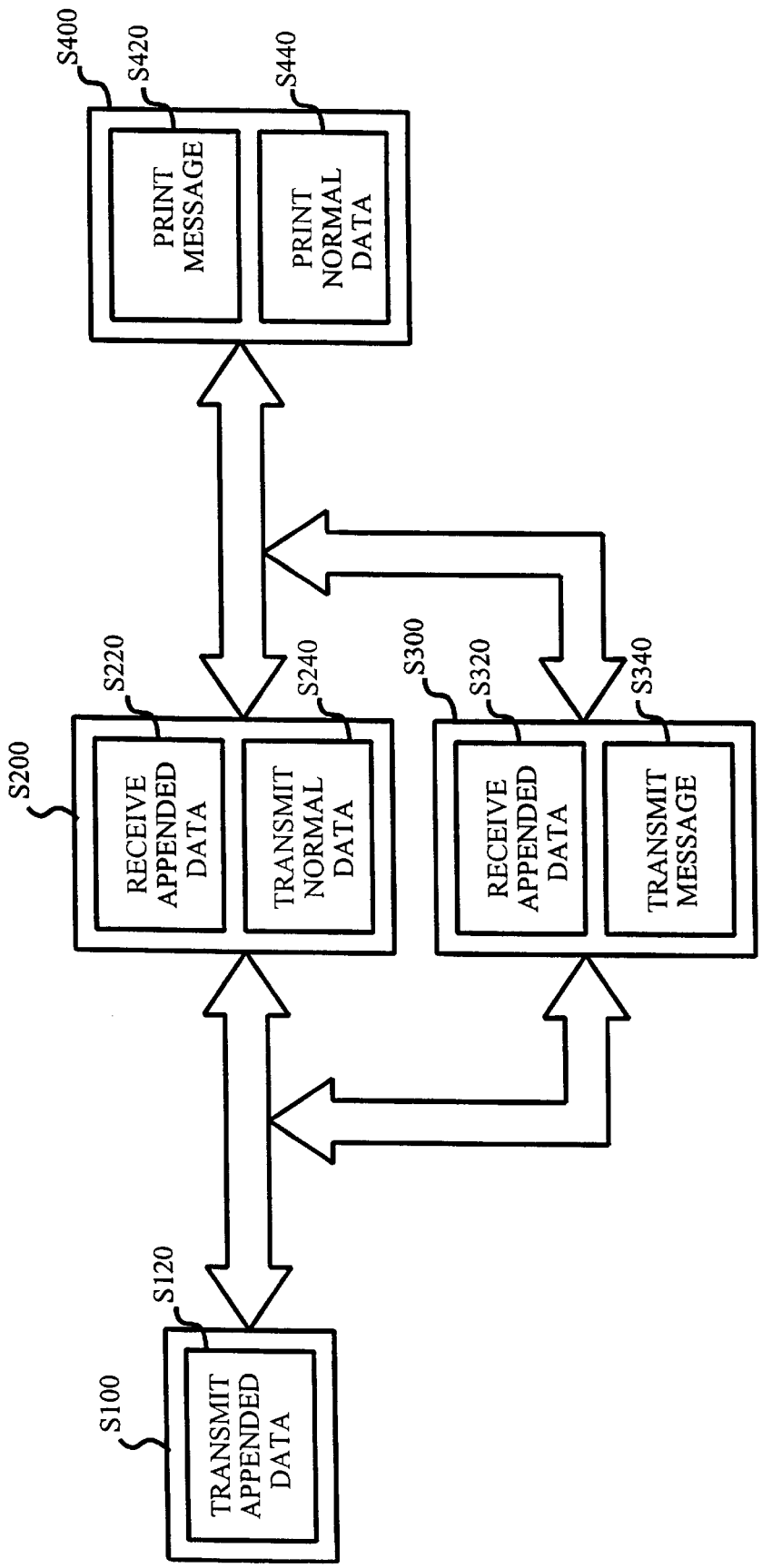
FIG. 1 is a top level flowchart of the functions performed in accordance with the method of the invention.
Figure 2:
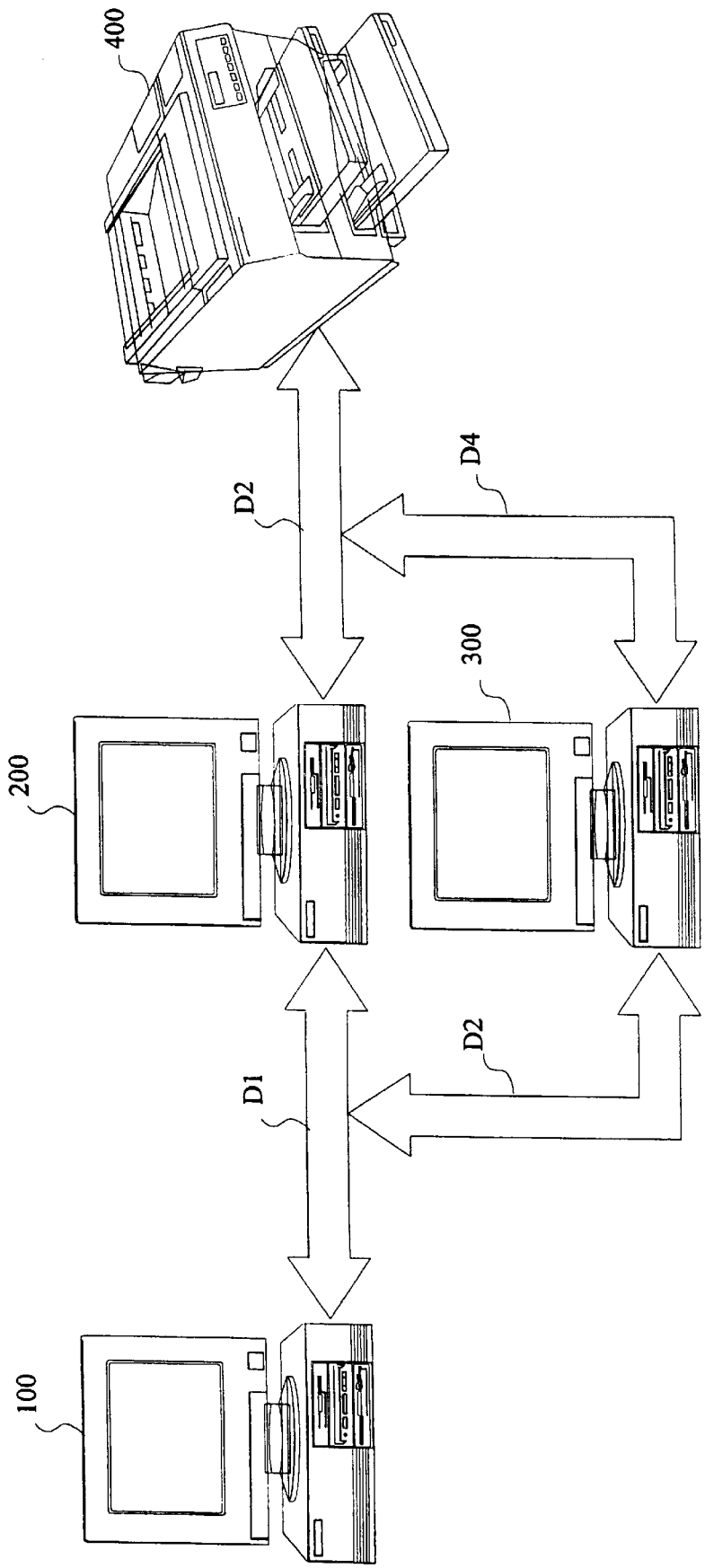
FIG. 2 is a top level block diagram illustrating the advisory computer system of the present invention in relation to pharmacy and third party computer systems and pharmacy computer system printing resources.

Referring now to the drawings, wherein like reference numerals designate identical or corresponding parts throughout the several views, and more particularly to FIGS. 1 and 2 thereof, there is illustrated a top level flowchart and a system block diagram of the respective method and system of the present invention including functions performed at a third party computer system 100 at step S100, functions performed at a pharmacy computer system 200 at step S200, functions performed at an advisory computer system 300 at step S300, and functions performed at a the pharmacy computer system's printing resources 400 at step S400.

Referring to FIGS. 1 and 2, at step S120, data is transmitted from the third party computer system 100 along with appended customer specific information, such as reminders to take other medication or to schedule a physical, etc., to the pharmacy computer system 200 over a data link D1, such as a parallel, serial, or modem data link, etc. The transmitted data is received at the pharmacy computer system 200 and the advisory computer system 300 at respective steps S220 and S320, over the data link D1 and a corresponding data link D3, such as a parallel, a serial, or a modem data link, etc. Optionally, at step S320, the transmitted data may be received by the advisory computer system 300 after passing through the pharmacy computer system 200 via a data link D2 and a corresponding data link D4, such as a parallel data link, a serial data link, a modem data link, etc.

At step S240, the pharmacy computer system 200 transmits normal data, such as label information, drug type, etc. to the pharmacy computer system's printing resources 400 over the data link D2. If the data transmitted from the third party computer system 100 is being intercepted after passing through the pharmacy computer system 200 by the advisory computer system 300, the normal data transmitted by the pharmacy computer system 200 at step S240 would also include the patient-specific information appended by the third party computer system 100. After the advisory computer system 300 either intercepts the transmitted data before reaching the pharmacy computer system 200 or after passing through the pharmacy computer system 200 at step S320, the advisory computer system 300 transmits a generated advisory message to the pharmacy computer system's printing resources 400 at step S340.

As previously discussed, the advisory computer system 300 includes a hardware interface 328 (see FIG. 3) for performing printing mediation to resolve printer conflicts between the advisory computer system 300 and the pharmacy computer system 200 using methods and/or systems, for example, as are known in the art or as described in commonly owned U.S. patent application Ser. No. 08/764,139. The pharmacy computer system's printing resources 400 print the advisory message generated and transmitted by the advisory computer system 300 and/or the normal data transmitted from the pharmacy computer system 200 at steps S420 and S440, respectively. It is noted that, in the preferred embodiment of the invention, the third party computer system 100, the pharmacy computer system 200, and the advisory computer system 300 typically use modem, parallel, and/or serial data transmission formats with appropriate logic and/or software functions provided in hardware interface 328 of the advisory computer system 300—for example, as is described in commonly owned U.S. patent application Ser. No. 08/764,139.

Figure 3:
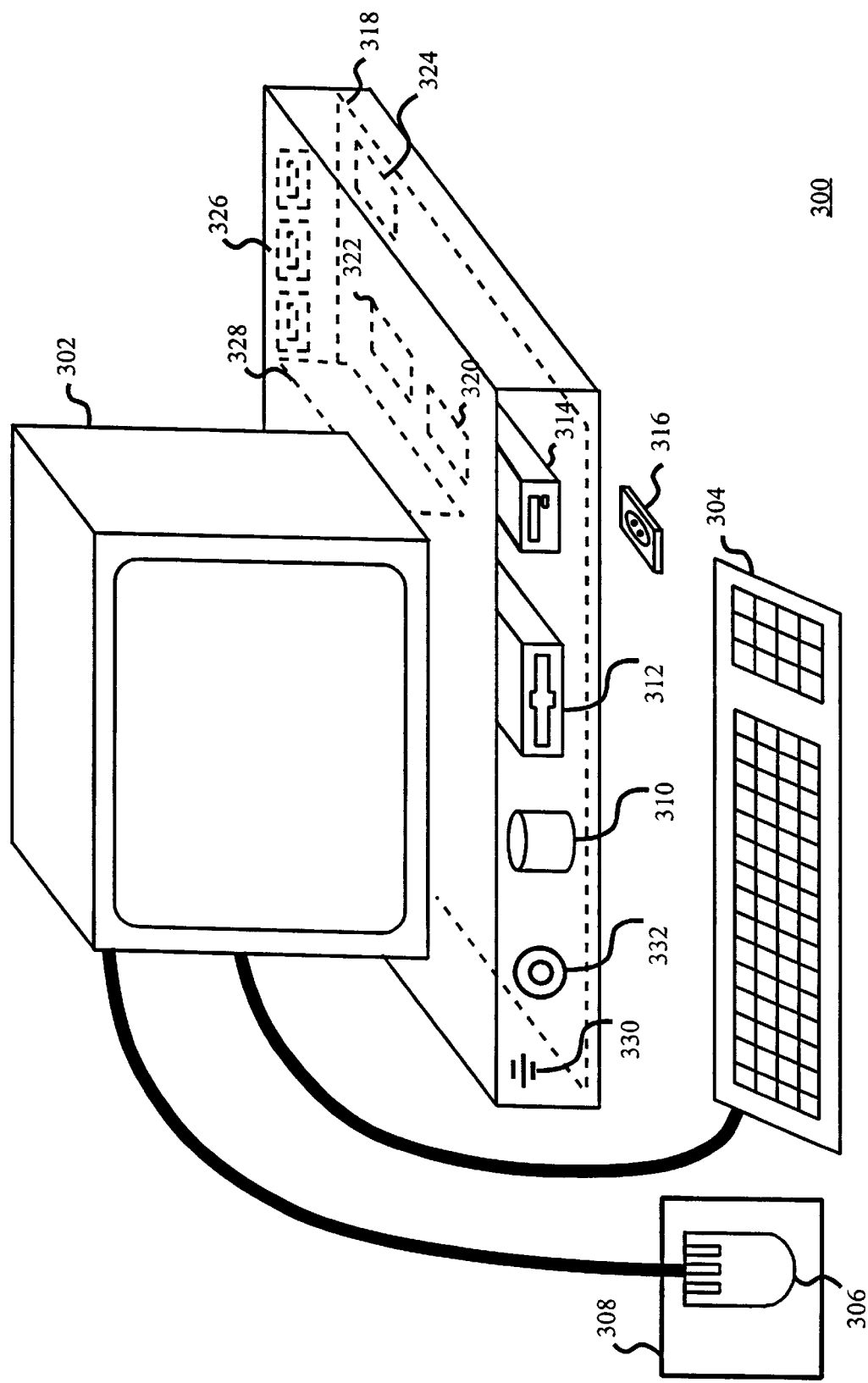
FIG. 3 is a detailed diagram illustrating details of the advisory computer system of FIG. 2.

In FIG. 3, the advisory computer system 300 is shown. It includes a display device 302, such as a conventional display device or a touch screen monitor with a touch-screen interface; a keyboard 304; a pointing device 306, such as a mouse, a mouse pad 308, or a digitizing pad; a hard disk 310; a floppy drive 312; a tape or CD ROM drive 314 with tape or CD media 316; and a mother board 318. The motherboard 318 includes a processor 320; a RAM 322; a ROM 324; I/O ports 326 which are used to couple to the third party computer system 100 and to the pharmacy computer system 200; the previously mentioned hardware interface 328 for performing specialized hardware/software functions, such as modem interfacing, serial-to-parallel and parallel to serial conversion, printer conflict mediation, sound processing, image processing, etc.; a microphone 330; and a speaker or speakers 332. In addition, the third party computer system 100 and the pharmacy computer system 200 also include any combination of the above described features and/or components of the advisory computer system 300.

Figure 4:
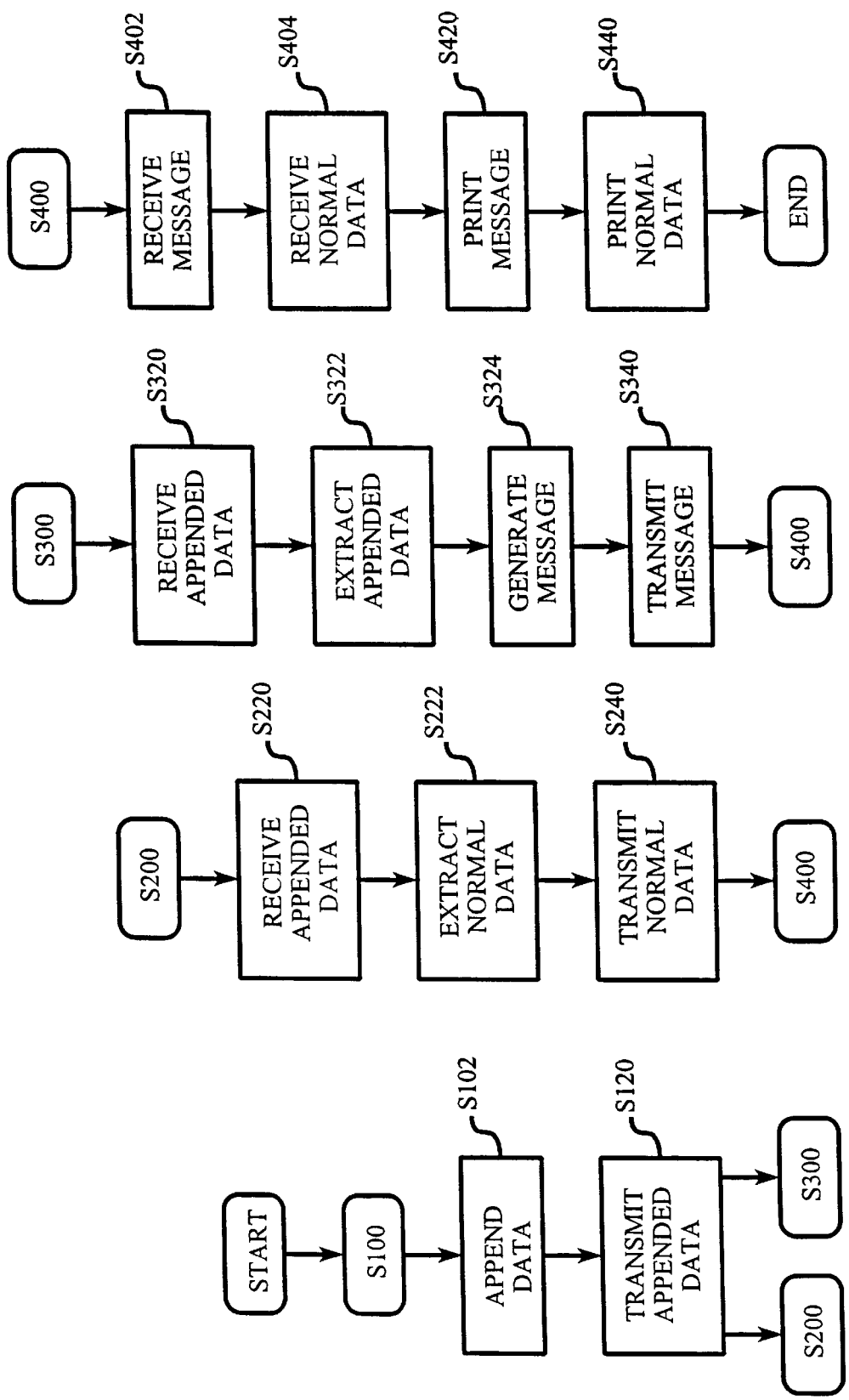
FIG. 4 are detailed flowcharts of the functions performed in FIG. 1 in accordance with the method of the invention.

The details of the operation of the system and method according to the present invention will now be described with reference to the flowchart of FIG. 4 and FIGS. 1–3. In FIG. 4, the third party computer system 100 appends the patient-specific information, such as personalized messages, appointment reminders, etc., to the normally transmitted data, such as the NDC, etc., at step S102. The patient-specific information may be appended in various forms—including, for example, appending the patient-specific information in unused fields, added fields, etc. of the normally transmitted data. Next, the appended data is transmitted from the third party computer system 100 to the pharmacy computer system 200 at step S120. As previously discussed, the advisory computer system 300 passively monitors the data transmitted by the third party computer system 100 via the data link D3.

After the data is transmitted by the third party computer system 100, the transmitted data is received by the pharmacy computer system 200 at step S220, and the normal data, such as the NDC, etc., is extracted by the pharmacy computer system 200 at step S222. The extraction step may include simply ignoring the appended patient-specific information in the unused or added fields of the normal data. Next, the extracted normal data is transmitted to the pharmacy computer system's printing resources 400 at step S240. As previously discussed, if the advisory computer system 300 monitors the transmitted data from the third party computer system 100 after the transmitted data passes through the pharmacy computer system 200, the data transmitted at step S240 by the pharmacy computer system 200 would include the normal data along with the appended patient-specific information.

The data transmitted, including the appended patient-specific information either transmitted by the third party computer system 100 or passing through the pharmacy computer system 200, is passively intercepted and received by the advisory computer system 300 at step S320. The appended patient-specific information is extracted by the advisory computer system 300 at step S322 and is used by the advisory computer system 300 to generate a patient-specific advisory message. Optionally, each different combination of information (such as the NDC, the age of the patient, the gender of the patient, whether the prescription is new or a refill, and the payer) may be used to trigger generation of a different advisory message, for example, as is described in commonly owned U.S. patent application Ser. No. 08/764,139, along with the patient-specific information provided by the third party computer system 100. The various combinations selected to trigger a message are stored in a database, such as the hard disk 310 of the advisory computer system 300 or to trigger a matrix associated with the advisory computer system 300. In the latter case, the trigger matrix is queried to determine which, if any, advisory messages are to be printed, for example, as is described in commonly owned U.S. patent application Ser. No. 08/764,139. The advisory message is generated by the advisory computer system 300 at step S324 and is transmitted to the pharmacy computer system's printing resources 400 at step S340.

The pharmacy computer system's printing resources 400 receive the messages transmitted by the advisory computer system 300 or the pharmacy computer system 200 at steps S402 and S404, and it prints the respective information at steps S420 and S440. The received messages may be messages that are normally transmitted by the pharmacy computer system 200 and received by the pharmacy computer system's printing resources 400 at step 404. Such received messages are not acted upon by the advisory computer system 300, and they are printed by pharmacy computer system's printing resources 400 at step S440. Alternatively, the received messages may be the patient-specific advisory messages transmitted by the advisory computer system 300 at step S340 and received by the pharmacy computer system's printing resources 400 at step 402. Such received message are printed by the pharmacy computer system's printing resources 400 at step S420. In this way, the normal printing functions performed by the third party computer system 100 via the pharmacy computer system 200 and the pharmacy computer system's printing resources 400 are not interrupted by the printing of the advisory messages from the advisory computer system 300.

Figure 5:
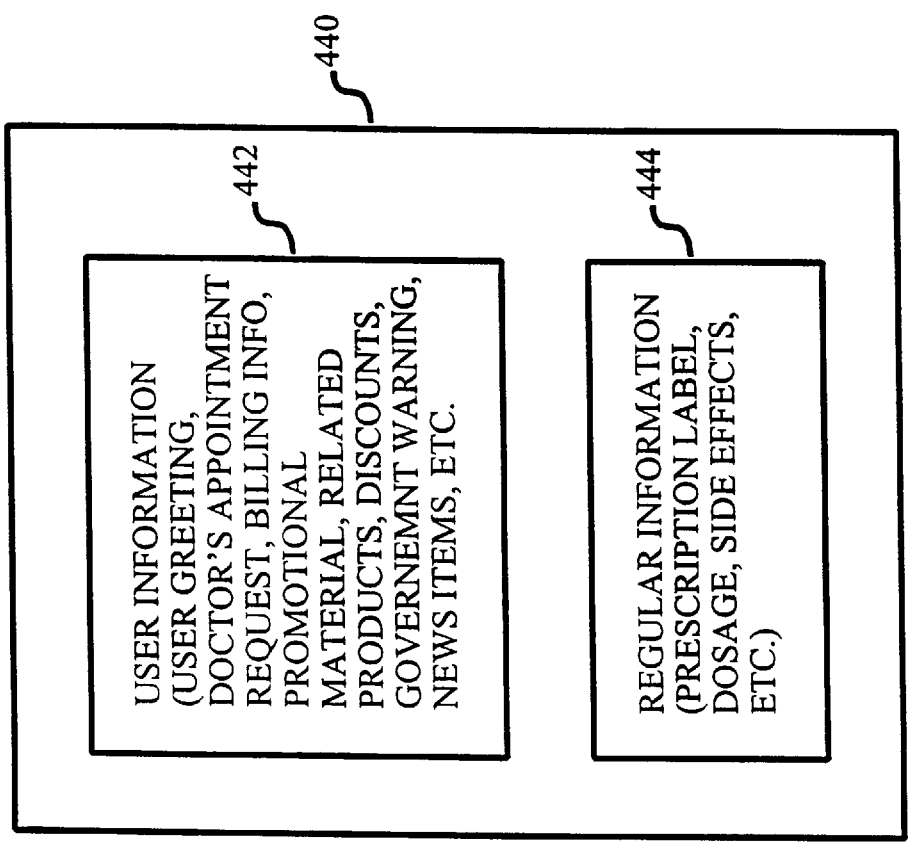
FIG. 5 is an illustration of the contents of a generated advisory message, according to the present invention.

An example of the contents of an advisory message 440 printed by the pharmacy computer system's printing resources 400 in response to data transmitted from the advisory computer system 300 is shown in FIG. 5. In FIG. 5, the advisory message 440 includes patient-specific information 442 and regular information 444. The patient-specific information 442 includes, for example, a greeting, a doctor's appointment reminders, billing information, promotional material, information concerning related products, discounts, coupons, government warnings, and news items. The regular information includes, for example, a prescription label, dosage information, information concerning side effects, etc. The advisory message 440 can be in the form of a patient-customized newsletter, and it can be delivered to the patient by the pharmacist. Studies have shown that patients regularly use pharmacists as a source of medical information since pharmacists are believed act objectively for the patient's best interests. Accordingly, having the advisory information presented to a patient by his or her pharmacist is a reliable and effective method of providing health advisory information as compared to conventional methods, such as mass mailings, targeted mailings, etc.

The invention represents a significant advance in the field of point-of-sale systems in the pharmacy environment. More specifically, the invention provides for distribution of patient specific information to pharmacy patients, taking into account information provided by interested third parties, such as HMOs and PPOs, and optionally important factors such as age, gender, prescription status, and payer identity, as well as the identification of the drug being dispensed. Furthermore, the invention achieves these goals without major modification of existing third party and pharmacy computer systems. An added advantage is that, because the system of the invention taps passively into data streams from the third party computer system either entering or leaving the pharmacy computer system, any malfunction of the invention has no affect on the basic operation of the third party or pharmacy computer systems, which can continue to process prescriptions and print labels.

The ability of the invention to provide targeted information to patients can be extended to the provision of product samples that are similarly targeted, based on the same data stream entering and/or leaving of the pharmacy system.

Yet another advantage of the invention is that, if the advisory computer 300 is connected to a network of similar computers, advisory messages can be directed to pharmacists over this network and printed on the pharmacy printer.

Although the preferred embodiment of the invention is described in terms of a third party computer system 100, a pharmacy computer system 200, and an advisory computer system 300 employing parallel, serial, and/or modem data transmission formats, as will be apparent to those skilled in the computer art, other forms of data transmission formats may be used, such as network, coaxial cable, fiber optic, wireless, etc., by modifying the hardware interface 328 of the advisory computer system 200 to include appropriate interface logic and/or software functions.

The present invention includes a computer program product for implementing the processes of the present invention (e.g., as shown in FIGS. 1 and 4). The computer program product may be on a storage medium including instructions and/or data structures which can be used to program the advisory computer system 300 and the third party computer system 100 (FIGS. 2 and 3) to perform a process of the invention. The storage medium can include, but is not limited to, any type of disk including floppy disks, optical discs, CD-ROMs, and magneto-optical disks; ROMs; RAMs; EPROMs; EEPROMs, magnetic or optical cards; or any type of media suitable for storing electronic instructions (e.g., the hard disk 310, the floppy drive 312, the tape or CD ROM drive 314 with the tape or the CD media 316, the RAM 322, and the ROM 324 of the advisory computer system 300 and similar devices in the third party computer system 100). In addition, the ROM and RAM devices of the advisory computer system 200 and the third party computer system 100 are used to implement data structures for storing the patient-specific information, information normally transmitted by the third party computer system 200, information received by the advisory computer system 200, and the advisory message generated by the advisory computer system 300. However, as will be readily apparent to those skilled in the art, this invention may also be implemented by the preparation of application-specific integrated circuits or by interconnecting an appropriate network of conventional component circuits, Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for generating advisory messages to pharmacy patients, said method comprising the steps of:
   (a) appending patient-specific information to a data record:
      (i) containing normally transmitted information
      (ii) transmitted between a third party computer and a pharmacy computer during a pharmacy transaction;
   (b) capturing the data record transmitted to the pharmacy computer as the data record is received by the pharmacy computer or after the data record is transmitted from the pharmacy computer;
   (c) extracting the patient-specific information from the captured data record;
   (d) generating an advisory message based on the extracted patient-specific information; and
   (e) transmitting the generated advisory message to a pharmacy printer.

2. The method of claim 1 wherein the step of appending patient-specific information comprises appending any one of a patient greeting, a doctor's appointment reminder, billing information, promotional materials, information concerning related products, information concerning related discounts, government warnings, and news items.

3. The method of claim 1 wherein the step of appending patient-specific information comprises appending the patient-specific information to a data record containing normally transmitted information including any one of a prescription label, dosage information, and information concerning side effects.

4. The method of claim 1 wherein the step of generating an advisory message based on the extracted patient-specific information comprises generating an advisory message in the form of a newsletter.

5. A system for generating advisory messages to pharmacy patients during pharmacy transactions with a pharmacy computer having a pharmacy printer, said system comprising:
   (a) a third party computer configured to append patient-specific information to a data record:
      (i) containing normally transmitted information
      (ii) transmitted between the third party computer and the pharmacy computer during the pharmacy transaction and
   (b) an advisory computer configured to:
      (i) capture the data record transmitted to the pharmacy computer as the data record is received by the pharmacy computer or after the data is transmitted from the pharmacy computer;
      (ii) extract the patient-specific information from the captured data record;
      (iii) generate an advisory message based on the extracted patient-specific information; and
      (iv) transmit the generated advisory message to the pharmacy printer.

6. The system of claim 5 wherein the patient-specific information comprises any one of a patient greeting, a doctor's appointment reminder, billing information, promotional materials, information concerning related products, information concerning related discounts, government warnings, and news items.

7. The system of claim 5 wherein the normally transmitted information includes any one of a prescription label, dosage information, and information concerning side effects.

8. The system of claim 5 wherein the advisory message is in the form of a newsletter.

9. The system of claim 5 further comprising a memory containing a data structure for storing information relating to said pharmacy transactions, said memory comprising:
   (a) fields which store said patient-specific information;
   (b) fields which store said normally transmitted information; and
   (c) fields which store said generated advisory message.

10. The system of claim 9 wherein the fields of said memory which store the patient-specific information comprise fields which store any one of a patient greeting, a doctor's appointment reminder, billing information, promotional materials, information concerning related products, information concerning related discounts, government warnings, and news items.

11. The system of claim 9 wherein the fields of said memory which store the normally transmitted information comprise fields which store any one of a prescription label, dosage information, and information concerning side effects.

12. The system of claim 9 wherein the fields of said memory which store the generated advisory message comprise fields which store any one of a patient greeting, a doctor's appointment reminder, billing information, promotional materials, information concerning related products, information concerning related discounts, government warnings, news items, a prescription label, dosage information, and information concerning side effects.

13. A computer program product comprising a computer storage medium having a computer program code mechanism embedded in said computer storage medium for causing a computer to generate an advisory message, said computer program code mechanism comprising:

(a) a first computer code device configured to append patient-specific information to a data record:
  (i) containing normally transmitted information
  (ii) transmitted between a third party computer and a pharmacy computer during a pharmacy transaction;

(b) a second computer code device configured to capture the data record transmitted to the pharmacy computer as the data record is received by the pharmacy computer or after the data record is transmitted from the pharmacy computer;

(c) a third computer code device configured to extract the patient-specific information from the captured data record;

(d) a fourth computer code device configured to generate an advisory message based on the extracted patient-specific information; and (e) a fifth computer code device configured to transmit the generated advisory message to a pharmacy printer.

14. The computer program product of claim 13 wherein the patient-specific information comprises any one of a patient greeting, a doctor's appointment reminder, billing information, promotional materials, information concerning related products, information concerning related discounts, government warnings, and news items.

15. The computer program product of claim 13 wherein the normally transmitted information includes any one of a prescription label, dosage information, and information concerning side effects.

16. The computer program product of claim 13 wherein the advisory message is in the form of a newsletter.

* * * * *